US00PP16282P2

(12) United States Plant Patent
Olesen et al.

(10) Patent No.: US PP16,282 P2
(45) Date of Patent: Feb. 21, 2006

(54) COMPACT FLORIBUNDA ROSE PLANT NAMED 'POULAC005'

(50) Latin Name: ***Rosa* hybrid**
Varietal Denomination: POULac005

(75) Inventors: L. Pernille Olesen, Fredensborg (DK); Mogens N. Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 10/342,687

(22) Filed: Jan. 14, 2003

(51) Int. Cl.
*A01H 5/00* (2006.01)

(52) U.S. Cl. ..... Plt./143
(58) Field of Classification Search ..... Plt./143, Plt./116
See application file for complete search history.

(56) References Cited

U.S. PATENT DOCUMENTS

| | | | | | |
|---|---|---|---|---|---|
| PP11,598 | P | * | 10/2000 | Olesen et al. | Plt./143 |
| PP12,557 | P2 | * | 4/2002 | Olesen et al. | Plt./149 |
| PP13,512 | P2 | * | 1/2003 | Carruth | Plt./143 |
| PP13,777 | P2 | * | 5/2003 | Zary | Plt./143 |
| PP14,048 | P2 | * | 8/2003 | Kralovetz | Plt./143 |

OTHER PUBLICATIONS

UPOV ROM GTITM Computer Database, GTI Jouve Retrieval Software 2003/05 Citation for 'POULac005'.*

* cited by examiner

*Primary Examiner*—Kent Bell
*Assistant Examiner*—W. C. Haas

(57) ABSTRACT

A new compact floribunda rose plant which has abundant, pink flowers and attractive foliage. The variety successfully propagates from softwood cuttings and is suitable for year round production in commercial glasshouses. This new and distinct variety has shown to be uniform and stable in the resulting generations from asexual propagation.

1 Drawing Sheet

Botanical classification: *Rosa* hybrid.
Variety denomination: 'POULac005'.
Commercial classification: Compact Floribunda.

SUMMARY OF THE INVENTION

The present invention constitutes a new and distinct variety of compact floribunda rose plant which originated from a controlled crossing between an unnamed seedling, not patented, and 'POULdrik' described and illustrated in U.S. Plant Pat. No. 12,557, issued on Apr. 23, 2002. The two parents were crossed and the resulting seeds were planted in a controlled environment. The new variety is named 'POULac005'.

The new variety may be distinguished from its pollen parent, 'POULdrik' created by the same inventors, by the following combination of characteristics:

1. 'POULdrik' has a petal count of 14 to 18 petals, while that of 'POULac005' is 25.
2. 'POULdrik' has a general tonality of Red Group 52C while that of 'POULac005' is a blend of Red Group 49A and Orange-Red Group 32C.
3. 'POULdrik' has a bloom diameter of 60 mm, while that of 'POULac005' is 70 to 80 mm.

The objective of the hybridization of this rose variety for commercial culture was to create a new and distinct variety with unique qualities, such as:

1. Uniform and abundant flowers;
2. Vigorous and compact growth;
3. Year-round flowering under glasshouse conditions;
4. Suitability for production from softwood cuttings in pots;
5. Durable flowers and foliage which make a variety suitable for distribution in the floral industry.

This combination of qualities is not present in previously available commercial cultivars of this type, known to the inventors, and distinguish 'POULac005' from all other varieties of which we are aware.

As part of their rose development program, L. Pernille Olesen and Mogens N. Olesen germinated the seeds from the aforementioned hybridization and conducted evaluations on the resulting seedlings in a controlled environment in Fredensborg, Denmark.

'POULac005' was selected by the inventors as a single plant from the progeny of the hybridization in April of 1995.

Asexual reproduction of 'POULac005' by cuttings and traditional budding was first done by L. Pernille and Mogens N. Olesen in their nursery in Fredensborg, Denmark in June of 1995. This initial and other subsequent propagations conducted in controlled environments have demonstrated that the characteristics of 'POULac005' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems of 'POULac005'. Specifically illustrated the drawing:

1. Stem showing branching and the attachment of leaves, buds, and peduncles;
2. Flower bud, partially opened bud, and open bloom;
3. Flower petals, detached;
4. Sepals, receptacle, and pedicel;
5. Stem as well as a bare stem exhibiting thorns;
6. Leaves.

DETAILED DESCRIPTION OF THE VARIETY

The following is a description of 'POULac005', as observed in its growth in a field nursery in Jackson County, Oreg. Observed plants are 2 years of age and were budded on to *Rosa multiflora* understock. Color references are made using The Royal Horticultural Society (London, England) Colour Chart, 1995, except where common terms of color are used.

Weather Data for Jackson County Oregon

| | May | June | July | August |
|---|---|---|---|---|
| Average High (F.) | 72.2 | 81.1 | 90.1 | 90.0 |
| Average Low (F.) | 43.8 | 49.9 | 54.9 | 54.6 |

For a comparison, several physical characteristics of the rose variety 'POULjoey', a rose variety from the same inventors described and illustrated in U.S. Plant Pat. No. 11,598 and issued on Oct, 24, 2000 are compared to 'POULac005' in Chart 1.

CHART 1

| | 'POULac005' | 'POULjoey' |
|---|---|---|
| General Tonality | Blend of Red Group 49A and Orange-Red Group 32C. | Blend of Orange-Red Group 31B and Red Group 39B. |
| Petal Count | 25 | 55 to 65. |
| Bloom diameter | 70 to 80 mm. | 50 to 60 mm. |

Parents: 'POULdrik'×an unnamed seedling.

FLOWER AND FLOWER BUD

Blooming habit: Recurrent.

Flower bud:

*Size.*—Upon opening, 28 mm in length from base of receptacle to end of bud. Diameter is normally 15 mm.

*Bud form.*—Long and high-centered.

*Bud color.*—As sepals unfold, Orange-Red Group 30D. At ¼ opening, Orange Group 28D.

*Sepals.*—Upper surface is Yellow-Green Group 144B, with areas of Yellow-Green Group 144A. Lower surface is Yellow-Green Group 144A, with anthocyanin intonations of Greyed-Orange Group 176A. Upper surface of sepals is moderately pubescent. Stipitate glands are present on sepal edges and undersides. Shape: Generally subulate. Sepal apex is cirrhose. Base is flat at union with receptacle. Size: 25 mm long×10 mm wide.

*Receptacle.*—Surface: Smooth. Shape: Funnel-shaped. Size: 4 mm (h)×6 mm (w). Color: Yellow-Green Group 144B.

*Pedicel.*—Surface: Somewhat rough with many fragrant stipitate glands. Length: 35 to 40 mm average length. Diameter is normally 2 to 3 mm. Color: Yellow-Green Group 144B. On plants grown under high light conditions, pedicel may exhibit intonations of Greyed-Red Group 181A. Strength: Strong.

*Borne.*—3 to 8 buds per stem.

*Anthocyanin.*—Peduncles are mottled with Greyed-Red Group 181A.

Flower bloom:

*Fragrance.*—Lightly spice scented.

*Duration.*—As a pot plant, flowers last from 8 to 10 days.

*Size.*—Average flower diameter is 70 to 80 mm when open. On average, flower depth is 27 mm.

*Form.*—

*Shape of flower when viewed from the side.*—Upon opening, upper part: Flat. Upon opening, lower part: Flat. Open flower, upper part: Convex. Open flower, lower part: Concave.

*Petalage.*—Average range: 25 petals under normal conditions with 3 to 6 petaloids.

Color:

*Upon opening, petals.*—Outermost petals: Outer Side: Orange Group 29B and C. Inner Side: Gradient between the basal zone color of Yellow Group 5A and the marginal zone color of Red Group 38A. Innermost petals: Outer Side: Orange Group 29A. Inner Side: Orange-Red Group 30D, some with a vertical streak of Yellow Group 6A.

*Upon opening, basal petal spots.*—Outermost petals: Outer Side: Yellow Group 7D. Inner Side: Yellow Group 6B. Innermost petals: Outer Side: Yellow Group 7B. Inner Side: Yellow Group 6D.

*After opening, petals.*—Outermost petals: Outer Side: Orange Group 24D. Inner Side: Red Group 29A graduating to Yellow Group 2A. Innermost petals: Outer Side: Orange Group 25D. Inner Side: Orange-Red Group 33D graduating to Yellow Group 6A.

*After opening, basal petal spots.*—Outermost petals: Outer Side: Yellow Group 3C. Inner Side: Yellow Group 3B. Innermost petals: Outer Side: Yellow Group 6A. Inner Side: Yellow Group 6A.

General tonality: On open flower, a blend of Red Group 49A and Orange-Red Group 32C. No change in the general tonality at the end of the $7^{th}$ day. Afterwards, general tonality is Red Group 49A.

Petals:

*Petal texture.*—Smooth.

*Petal reflex.*—Moderate.

*Petal edge.*—Entire.

*Shape.*—Deltoid.

*Size.*—Normally 25 mm long by 27 mm wide.

*Petaloids.*—Quantity: 3 to 6. Texture: Smooth. Size: 8 mm long; 13 mm wide. Color: Upper side is Orange-Red Group 32C, lower side is Orange-Red Group 32C.

*Thickness.*—Average.

*Arrangement.*—Not formal.

Reproductive organs:

*Pistils.*—Shape: Elongate. Apex is filamentous. Base broadens to enclose the ovary. Length: 10 mm long. Quantity: 20 to 25. Color: Yellow-Green Group 145C.

*Pollen.*—Color: Yellow-Orange Group 25A. Quantity: Scant.

*Anthers.*—Size: 2 to 3 mm long. Color: Yellow-Orange Group 16C. Quantity: 35 to 40.

*Filaments.*—Color: Yellow Group 9A. Length: 4 to 5 mm.

*Stigmas.*—Slightly superior in location relative to the length of the filaments and the height of the anthers. Color: Yellow-Green Group 145D.

*Styles.*—Color: Yellow-Green Group 145C.

*Seed formation.*—No hips observed.

PLANT

Plant growth: Vigorous, and bushy. Plants will acumulate 40 to 60 cm of vertical growth in one growing season. The average plant width is 50 cm.

Stems:

*Size*.—6 to 8 mm diameter. Normally 40 cm from the base of the plant to the flowering portion.

*Color*.—Young wood: Yellow-Green Group 144A. Older wood: Yellow-Green Group 144A.

*Internodes*.—Distance between nodes is normally 25 mm.

*Prickles*.—Incidence: 8 to 9 per 10 cm of stem. Size: Average length: 8 mm. Color: Greyed-Red Group 181A. Shape: Curved.

*Surface*.—Young wood: Rough. Older wood: Rough.

Plant foliage: Normal number of leaflets on normal leaves in middle of the stem: 5 leaflets.

*Leaf size*.—90 mm (l)×70 mm (w).

*Quantity*.—Normally 4 leaves per 10 cm of stem.

*Color*.—Upper Leaf Surface: Yellow-Green Group 146A. Lower Leaf Surface: Green Group 143A. Juvenile foliage: Upper Leaf Surface: Yellow-Green Group 144A. Lower Leaf Surface: Yellow-Green Group 144B.

Plant leaves and leaflets:

*Stipules*.—Quantity: 2 per compound leaf. Size: 10 to 15 mm long. Color: Yellow-Green Group 144A, Green Group 137A at margins. Presence of stipitate glands: On stipule edges. Shape: Nearly linear with outward extending apecies. Margin: Lightly serrated.

*Petiole*.—Length: 15 to 20 mm long. Diameter: 1 to 2 mm. Color: Yellow-Green Group 144A. Underneath: Yellow-Green Group 144A. Margins: Green Group 137A. Anthocyanin: Greyed-Red Group 181A.

*Rachis*.—Color: Yellow-Green Group 144A. Underneath: Yellow-Green Group 144A. Margins: Green Group 137A. Anthocyanin: Greyed-Red Group 181A.

*Leaflet*.—Size: Terminal leaflets are 35 to 40 mm long by 25 to 30 mm wide. Edge: Serrated. Shape: Base is rounded, while apex is acute. Texture: Thick. Glossiness: Glossy. Arrangement: Odd pinnate. Venation: Reticulate. Color is Yellow-Green Group 151B to Yellow-Green Group 145B.

Disease resistance: Average resistance to mildew, black spot, and *Botrytis* under normal growing conditions in Jackson County, Oreg.

Cold hardiness: 'POULac005' has been found to be resistant to damage from cold, heat and drought in USDA Zone 7.

It is claimed:

1. A new and distinct variety of rose plant of the compact floribunda class named 'POULac005', illustrated and described herein, due to its abundant, pink flowers, vigorous growth, compact habit, suitability for production from softwood cuttings in pots, and durable flowers and foliage which make the variety suitable for distribution in the floral industry.

* * * * *

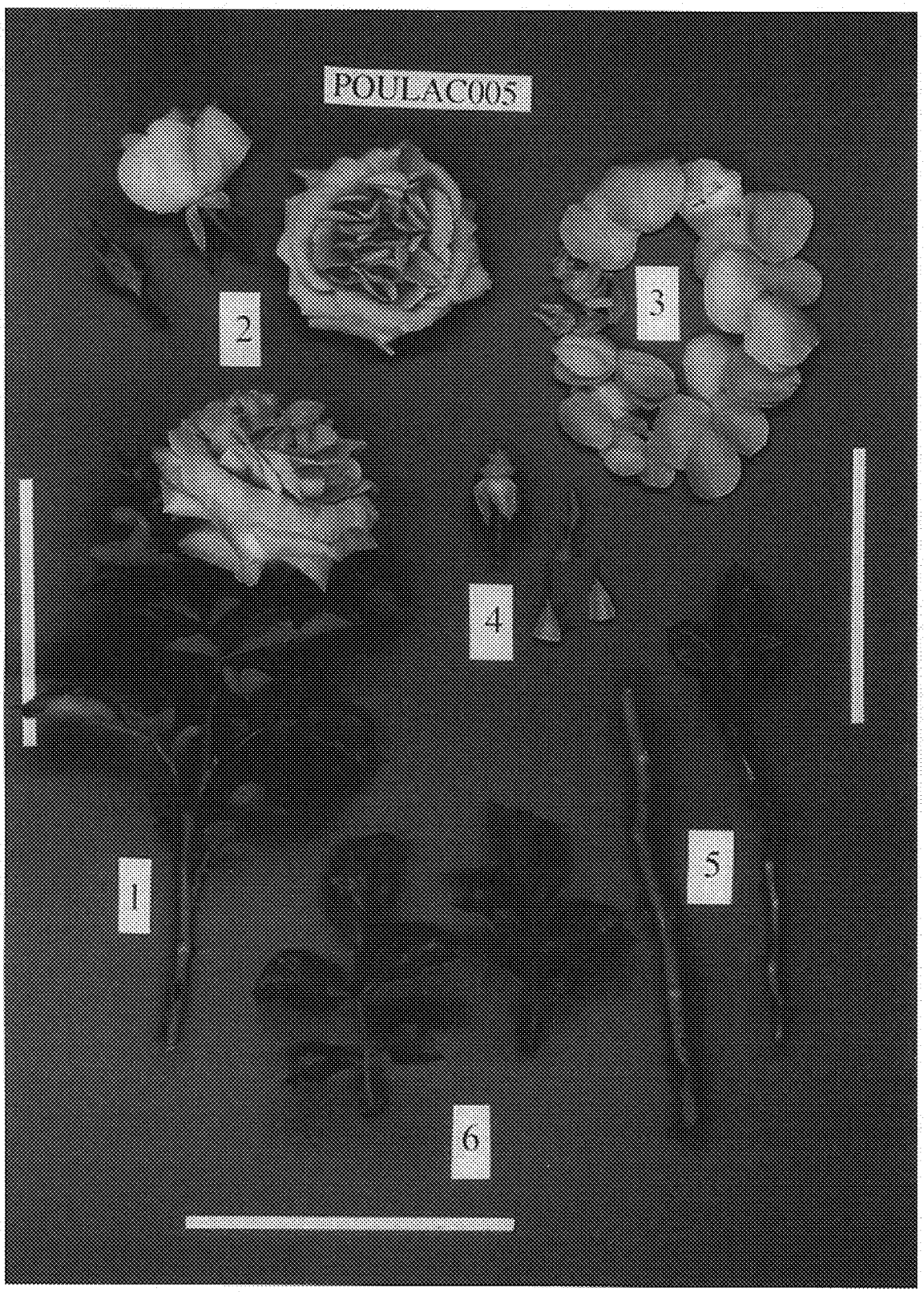
POULAC005
1
2
3
4
5
6